United States Patent [19]

Kaiser et al.

[11] Patent Number: 4,633,702
[45] Date of Patent: Jan. 6, 1987

[54] TORQUE AND FRICTION TESTER

[75] Inventors: Willard D. Kaiser, Grove City; Mark J. Koenig, Worthington; William K. LeBlanc, Mansfield, all of Ohio

[73] Assignee: The Shafer Valve Company, Mansfield, Ohio

[21] Appl. No.: 642,896

[22] Filed: Aug. 21, 1984

[51] Int. Cl.$^4$ .............. G01M 19/00; G01L 5/00; G01L 5/22; G01N 19/02
[52] U.S. Cl. ............................ 73/9; 73/168; 73/862.36; 73/862.54
[58] Field of Search .............. 73/9, 168, 847, 841, 73/846, 862.08, 862.19, 843, 862.09, 862.23, 862.36, 862.53, 862.54, 862.68

[56] References Cited

U.S. PATENT DOCUMENTS

| | | | |
|---|---|---|---|
| 2,582,784 | 1/1952 | Lumb et al. | 73/862.19 |
| 2,761,314 | 9/1956 | Vernier | 73/862.09 |
| 3,029,634 | 4/1962 | Schmitz | 73/862.09 |
| 3,059,464 | 10/1962 | Deane | 73/9 |
| 4,051,713 | 10/1977 | Bao et al. | 73/9 |
| 4,324,133 | 4/1982 | Stevenson | 73/862.09 X |
| 4,435,979 | 3/1984 | Gilgore | 73/168 |
| 4,498,336 | 2/1985 | Dalton | 73/168 |
| 4,543,814 | 10/1985 | Heilman | 73/862.08 |

FOREIGN PATENT DOCUMENTS

| | | | |
|---|---|---|---|
| 1091767 | 10/1960 | Fed. Rep. of Germany | 73/862.08 |
| 36782 | 3/1979 | Japan | 73/847 |
| 539232 | 12/1976 | U.S.S.R. | 73/847 |
| 540164 | 12/1976 | U.S.S.R. | 73/862.19 |
| 966520 | 10/1982 | U.S.S.R. | 73/168 |

Primary Examiner—Michael J. Tokar
Assistant Examiner—Tom Noland
Attorney, Agent, or Firm—Renner, Kenner, Greive, Bobak & Taylor

[57] ABSTRACT

An apparatus for measuring torque characteristics of devices (20, 73) includes a first shaft (19) having torque applied thereto by a first device (20) and a second shaft (41) having torque applied thereto by a second device (73). Sensing elements (31) are provided which detect the forces generated by the torque of the first and second shafts (19, 41) and produce electrical signals proportional to the forces detected. A first coupling device (25) transfers the forces generated by the torque from the first and second shafts (19, 41) to the sensing elements (31). A suspension mechanism (57) permits the second device (73) to move laterally independent in two spatial dimensions with respect to the first device (20) so as to minimize any effects from mechanical misalignment and the structural support frame (10). The apparatus can be adapted to measure frictional characteristics of devices (20, 73) by providing an actuator (93) for applying a torque to a third shaft (92). A second coupling device (95) transfers the rotational moment generated by the actuator (93) from the third shaft (92) to the first shaft (19). Sensing elements (31), contained within the second coupling device (95) measure the frictional characteristics of the first device (20) and compensates from mechanical misalignment between the actuator (93) and the first device (20).

19 Claims, 6 Drawing Figures

TORQUE AND FRICTION TESTER

TECHNICAL FIELD

The invention relates generally to a method and apparatus for measuring the torque and the frictional force of a machine or device. More specifically the invention relates to a novel method and apparatus for measuring the output torque and the frictional force of an actuator used to rotate a shaft which in turn drives a load device.

By way of example only and not limited hereto, many valves, particularly the larger, high pressure industrial valves, require actuators capable of producing torque values as high as 10,000,000 in-lb along the actuator output drive shaft. For purposes of production testing and selection of actuators for specific applications, it is necessary to determine the torque developed at the output shaft driven by the actuator and the frictional forces of the actuator when a load is connected to the shaft and the actuator is energized, such as when a valve shaft is connected to the actuator. It will be appreciated that the novel method and apparatus embodying the concept of the present invention hereinafter disclosed may be used in connection with any device which produces torque as one of its output characteristics.

BACKGROUND ART

The measurement of torque values, as for example, on a shaft driven by a valve actuator, is an expensive, time consuming and possibly inaccurate process which is dependent on many factors such as test stand alignment and geometry, welding and materials of the test stand and unknown friction of the testing system. Friction measurements may have to be done on a completely separate test stand which is a costly and time consuming inefficiency.

A conventional torque measurement system and method involves the use of a fixed, immovable test stand which may be a spool subtended by upper and lower flanges with a shaft welded to the lower flange and extending up through the spool and upper flange. The device to be tested is bolted to the upper flange with the upper end of the shaft being inserted into the device. Strain gauges, which produce electrical signals in proportion to shear forces acting thereon, are diametrically mounted on the shaft and strain gauges are also mounted on the periphery of the spool. In order to mount the gauges on the shaft, a window must be cut through the side of the spool.

Under theoretically ideal conditions the torque developed along the shaft by the device under test would be fully transferred and sensed by the strain gauges and the data could be interpreted using well-known stress-strain equations. However, the use of conventional welding techniques, spool materials, and the complicated geometry of the spool itself disrupts the stress uniformity and prevents accurate mathematical strain calculations. Therefore, interpretation of the strain gauge readings is difficult and inaccurate. Alignment of the device when it is bolted to the spool will also affect the stress distribution throughout the test stand. Calibration of the test stand can be done but such a process is costly and complicated. As a result, errors as high as 10-15% can be expected when measuring torque by such conventional methods.

It is appreciated that the friction characteristics of an actuator when energized and under a load are different from the friction characteristics of the same actuator when it is not so energized. To accurately determine the operating capabilities of an actuator, therefore, it is necessary to ascertain the friction characteristics of the actuator when it is energized and under a load. Inasmuch as the test shaft of the prior art test stand is fixed and the output shaft of the actuator cannot rotate when coupled thereto, the friction in the test system when the actuator is under a load cannot readily be determined.

It is, therefore, apparent that the state of the prior art is such that the need exists for a comprehensive method and apparatus which can accurately and economically measure the torque produced by a device and the frictional force of that same device when it is under a load condition, independent of test stand structural or material characteristics.

DISCLOSURE OF THE INVENTION

It is, therefore, the primary object of the present invention to provide a new and improved method and apparatus for measuring the torque produced by a device and for measuring the frictional force of the device under a load condition.

It is another object of the invention to minimize the effect of mechanical misalignment between the device under test and the apparatus.

It is yet another object of the invention to perform the torque and friction measurements on the same apparatus.

It is still another object of the invention to utilize only two conventional strain sensing elements to measure the torque produced by the device and only two additional conventional strain sensing elements to measure the frictional force of the device under a load condition.

It is an even further object of the invention to minimize any error induced by the apparatus when coupling the torque to the strain sensing devices.

It is yet another object of the present invention to provide an apparatus which automatically compensates for any misalignment between itself and the device under test.

It is yet a further object of the invention to measure the break-away friction and the dynamic friction of the device under test.

It is still a further object of the invention to provide a transducer unit which converts the electrical signals produced by the strain sensing elements to torque and friction readings on digital and analog panel meters.

These and other objects are accomplished by the improvements comprising the present invention, a preferred embodiment of which is disclosed herein by way of example as comprising the best known mode of carrying out the invention. Various modifications and changes in details of construction are comprehended within the scope of the appended claims.

In general, the present invention relates to an apparatus for measuring the torque characteristics of devices. Such apparatus includes a first device applying torque to a first shaft, a second device applying torque to a second shaft, sensing elements for detecting forces generated by the torque of the first and second shafts and providing electrical signals proportional thereto. The apparatus also includes a unique coupling mechanism for transferring the forces generated by the torque of the first and second shafts to the sensing elements and a novel suspension mechanism which permits the second device to be independently and freely movable in two dimensional space with respect to the first device.

The present invention also provides a unique apparatus for measuring the friction characteristics of devices. Such apparatus includes a first shaft having a torque applied thereto by a first device and an opposing torque applied thereto by a second device such that a zero resultant rotational moment is applied to the first shaft. A second shaft has a torque applied thereto by a third device. Sensor means are provided for detecting the forces generated by the torque of the third device and provides electrical signals proportional thereto. Means are likewise provided for transferring the force generated by the torque from the third device to the sensor means and the first shaft. Suspension means permit independent lateral movement of the second device and the third device with respect to the first device.

The present invention also relates to a method for measuring the torque characteristics of devices. Such a method employs the steps of mounting a first device to a stationary frame, applying torque to a first shaft with the first device, suspending a second device from the stationary frame such that the second device is permitted to move freely and independently in two dimensional space with respect to the first device, providing torque to a second shaft with the second device, coupling the forces generated by the torque of the first and second shafts to sensing elements, measuring these forces coupled to the sensing elements and providing electrical signals proportional to these measurements, and calculating therefrom the torque between the first and second shafts.

The present invention also provides a method for measuring the friction characteristics of devices. Such method includes the steps of mounting a first device to a stationary frame, and applying a torque from the first device to a first shaft. A second device is suspended from the stationary frame such that it is permitted to move laterally independent of the first device. An opposing torque from the second device is applied to the first shaft. The first device is restricted from rotating relative to the second device. A third device is suspended from the stationary frame such that it may move laterally independent of the first device and the second device; and, the third device applies a torque to a second shaft. The third device is restricted from rotating relative to the first device and the second device. The force generated by the torque applied to the second shaft is transferred to sensing elements and to the first shaft. The forces so transferred are measured and electrical signals proportional thereto are provided. These electrical signals are then used to determine the frictional characteristics of the devices being tested.

PREFERRED EMBODIMENT FOR CARRYING OUT THE INVENTION

Figure 1:
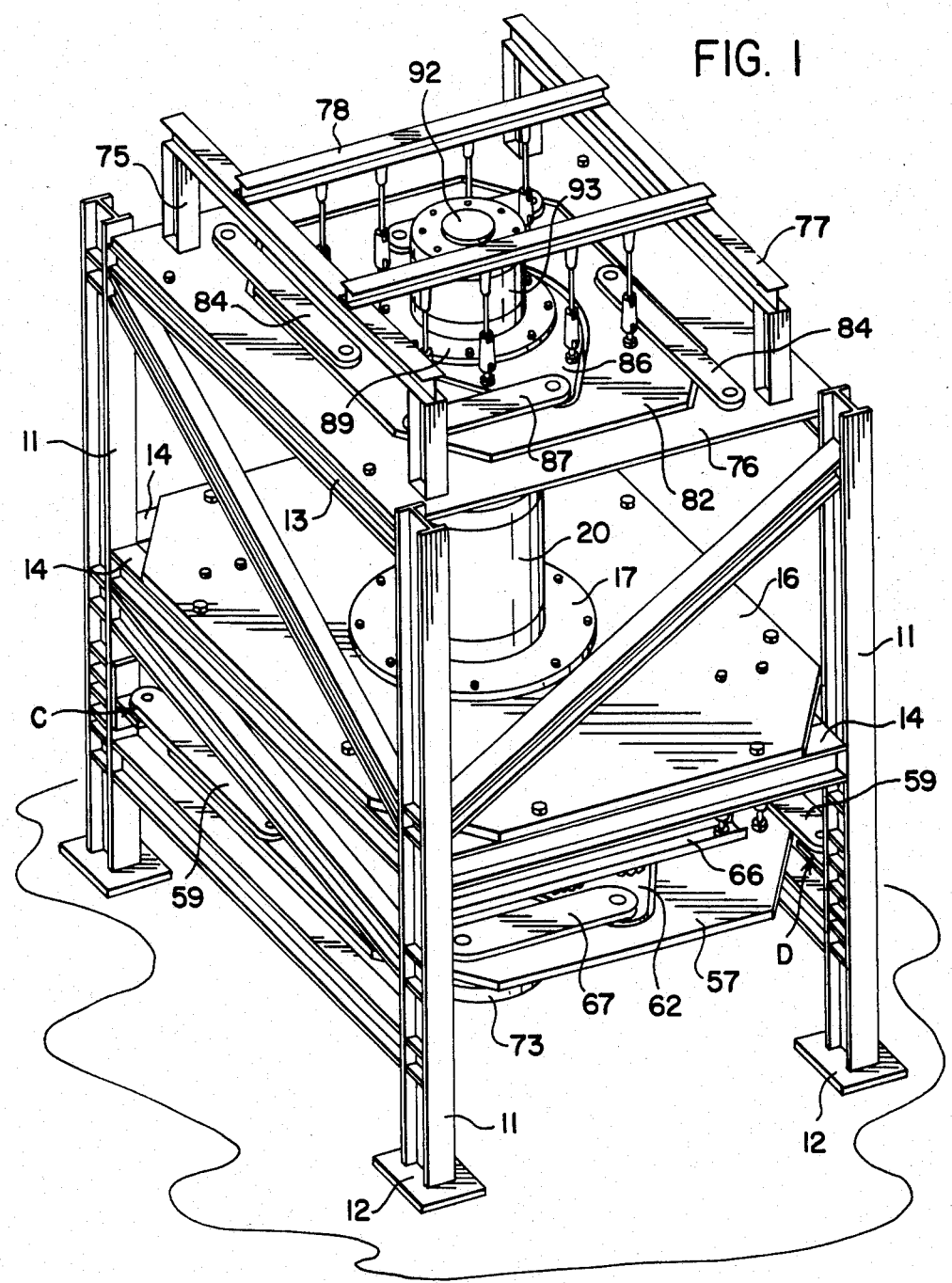
FIG. 1 is a somewhat schematic perspective view of the apparatus according to the concept of the present invention.
Figure 2:
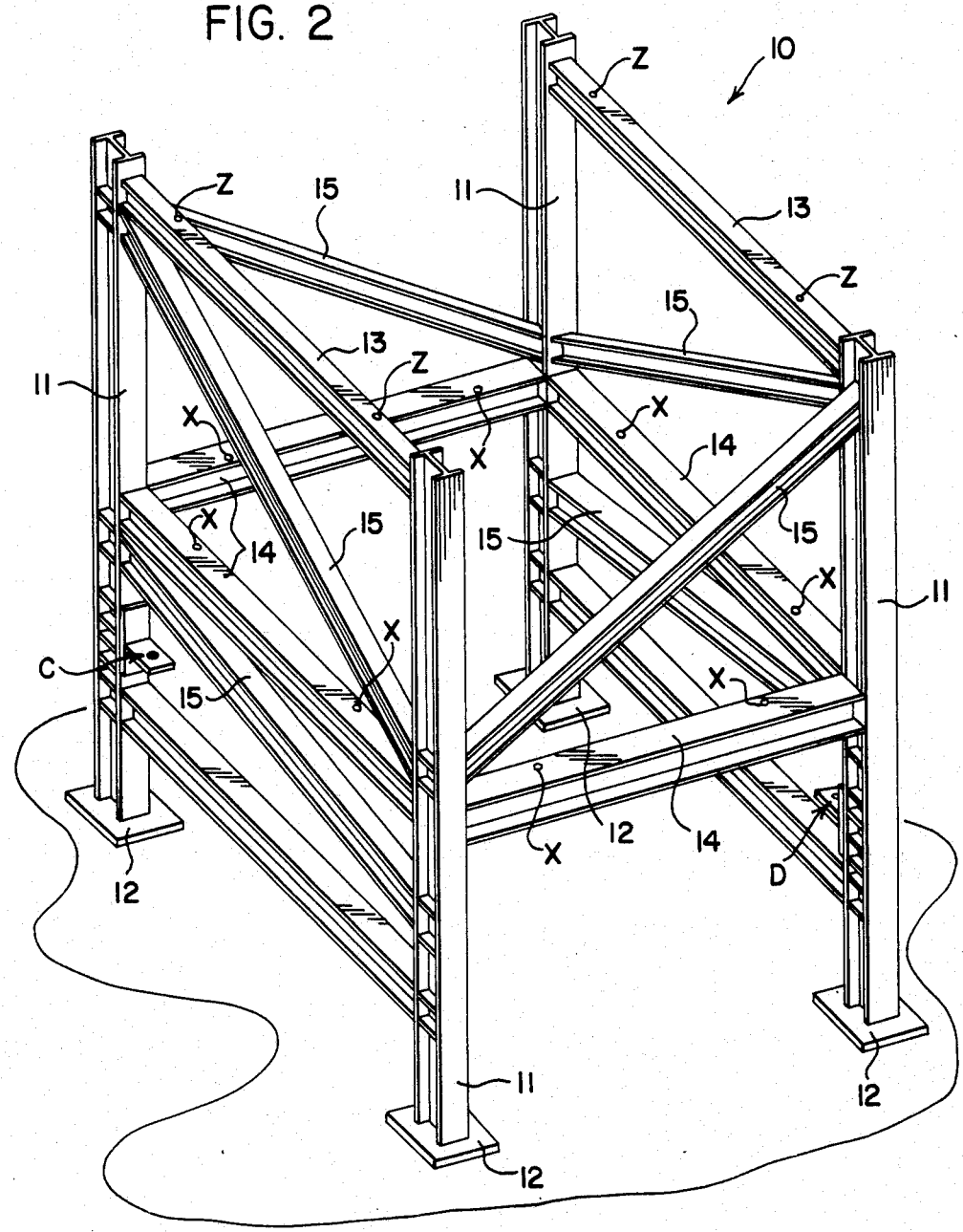
FIG. 2 is a somewhat schematic perspective view of the frame assembly portion of the apparatus according to the concept of the present invention.

The overall apparatus shown in FIG. 1 includes a main frame assembly best shown in FIG. 2 and generally indicated by the numeral 10. As shown in FIG. 1, frame 10 provides the structural support for the torque test assembly shown in FIG. 3 and the friction test assembly shown in FIG. 4 and includes the support posts 11 which may be conventional I-beams of sufficient and uniform length to support the entire apparatus. Posts 11 are vertically oriented and so disposed as to form the corners of an essentially cubic frame. Posts 11 can be mounted on a plurality of ground plates 12 by conventional methods such as welding. Plates 12 provide floor stability for frame 10. A plurality of upper support beams 13 are disposed at coincident heights near the top of posts 11 and are horizontally oriented in parallel relationship with each other between their respective support posts 11. A plurality of lower support beams 14 are horizontally disposed at a uniform height near the middle of support posts 11. There may be four lower beams, one between each pair of support posts 11 which form a side of the cubic frame. Thus, the four lower beams 14 form a square support ring centrally disposed within frame 10. A plurality of diagonally oriented crossbeams 15 are disposed between support posts 11 as best exemplified in FIG. 2 and provide structural support to frame 10 by methods well known to one of ordinary skill in the art. All crossbeams 15 and support beams 13, 14 may be conventional I-beams affixed by methods well known to one of ordinary skill in the art such as welding. It is contemplated that many different types of main frames 10 can be used which would provide adequate support for the remaining elements of the apparatus with frame 10 depicted in FIG. 2 being only exemplary.

Figure 3:
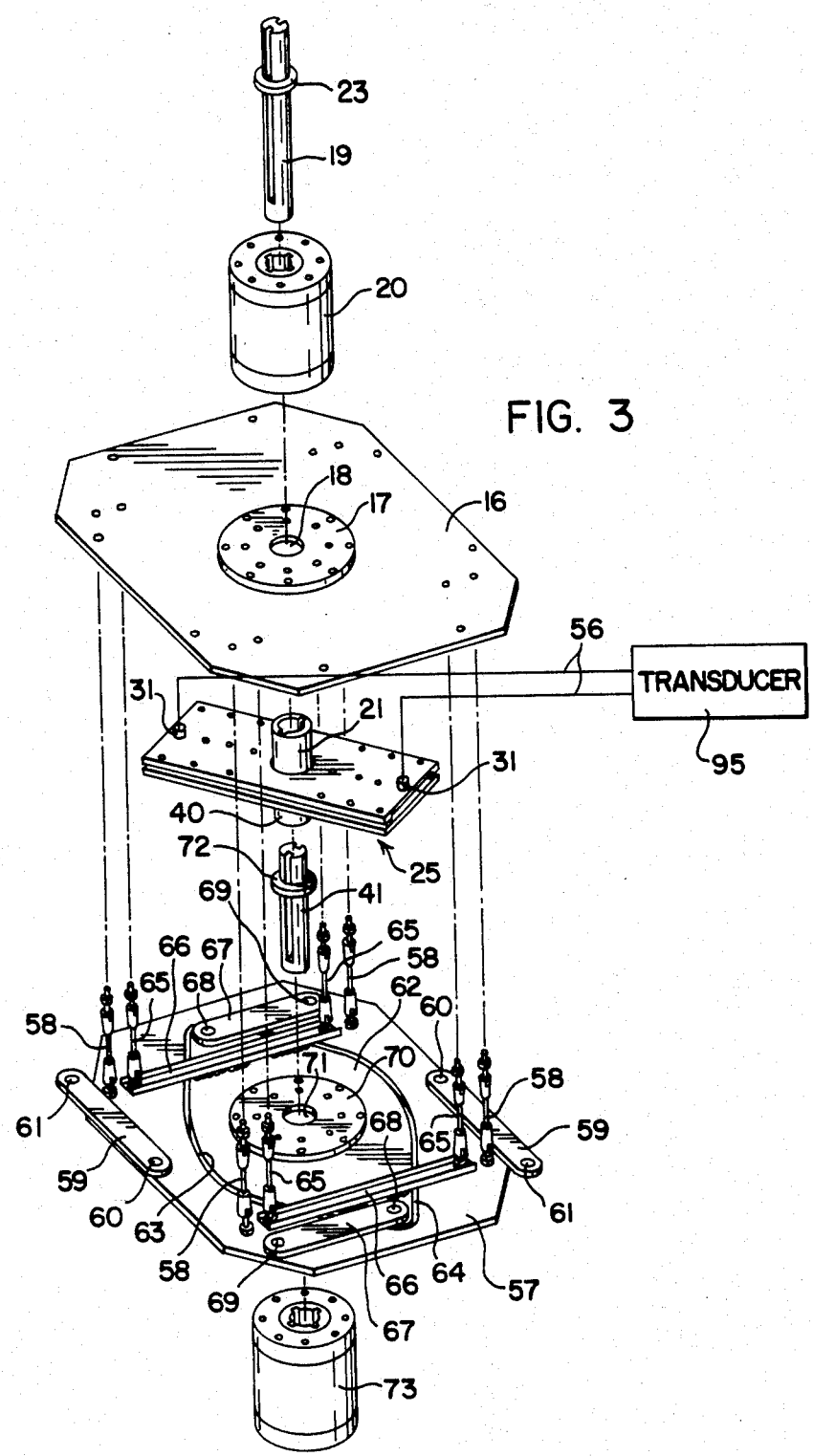
FIG. 3 is a somewhat schematic and partially exploded view of the torque test assembly portion of the apparatus according to the concept of the present invention.

Frame 10, and specifically lower support beams 14, carries a fixed torque plate 16 by any convenient means such as bolts at the points labeled "X" (FIG. 2), such that plate 16 is disposed horizontally on beams 14 between support posts 11 (FIG. 1). As depicted in FIG. 3, concentrically affixed to plate 16 is torque actuator mounting ring 17. Ring 17 and plate 16 each have a concentrically located, generally circular orifice 18 of sufficient diameter to accommodate an upper torque shaft 19.

An upper torque device 20 is affixed to the top of mounting ring 17 by any suitable means such as bolts. For exemplary purposes only, torque device 20 is depicted as a typical valve actuator manufactured by Shafer Valve Company, Mansfield, Ohio; it will be appreciated, however, that many different types of torque actuators and devices which produce torque may be tested by the apparatus and method herein disclosed. The particular device chosen will determine the particular mounting arrangement used to affix device 20 to plate 16.

Figure 4:
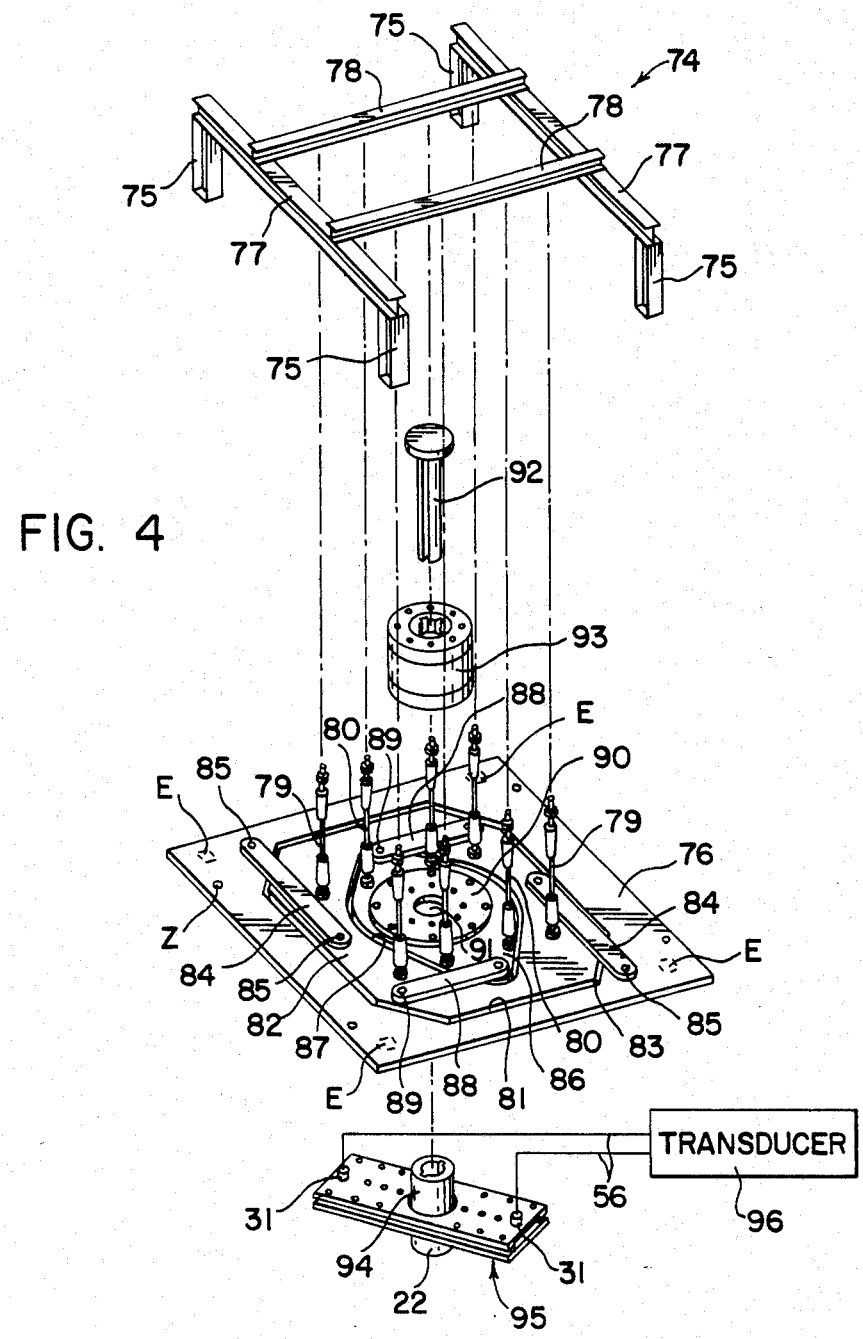
FIG. 4 is a somewhat schematic and partially exploded view of the friction test assembly portion of the apparatus according to the concept of the present invention.

Shaft 19 is of sufficient length to extend through device 20, through orifice 18, and into a torque sensor bar hub 21, terminating therein. Shaft 19 also protrudes up from device 20 and inserts into a friction lower saddle hub 22 (FIG. 4). Shaft 19 may include stop collar 23 so that when shaft 19 is inserted into device 20, collar 23 rests on the top of device 20 and prevents shaft 19 from extending too far into hub 21. Thus, a sufficient length of shaft 19 can be extended above device 20 and allows vertical adjustment of hub 22 and hub 21 along shaft 19. Shaft 19 may be keyed as with guides 24 (FIG. 5) which mechanically interlock shaft 19 with device 20 and hubs 21 and 22, by methods well known to one of ordinary skill in the art.

Figure 5:
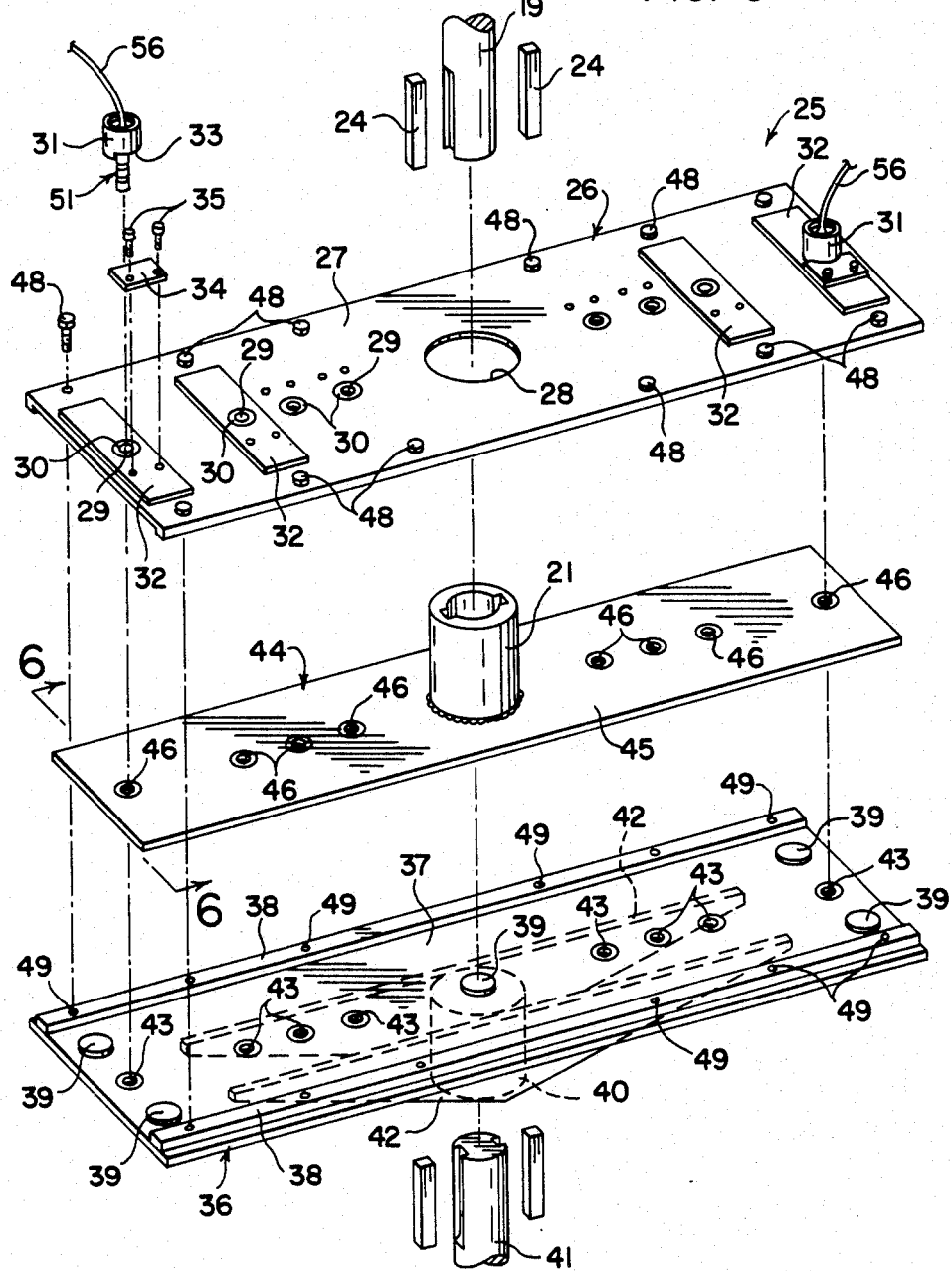
FIG. 5 is an exploded view of the torque sensor bar assembly shown in FIG. 3.

As described previously, when the apparatus in FIG. 3 is assembled, shaft 19 extends down into and terminates at hub 21. Hub 21 is part of a torque sensor bar assembly generally indicated by the numeral 25 in FIG. 3 and shown in detail in FIG. 5 which is an exploded view thereof. Referring to FIG. 5, an upper saddle assembly is generally indicated by the numeral 26. Saddle 26 includes a plate 27, "C" shaped in section, with a circular cutout 28 in the center of plate 27 of sufficient diameter to allow torque sensor bar hub 21 to protrude therethrough when sensor bar assembly 25 is fully assembled (as in FIG. 3). Plate 27 further includes a series of reamed holes 29 located on the lateral centerline of plate 27 and which may have hardened bushings 30 inserted therein. The bushings are of just sufficient size to allow selective insertion of two load cells 31 one of which, for clarity in FIG. 5, is shown in an exploded view on the left side with the right side load cell 31 and its associated mounting structure being shown as fully assembled. A description of only the left side mounting structure will be given, recognizing that all the load cell mounting structures may be of the same construction.

Referring to the left side exploded view of FIG. 5, a plurality of rectangular plates 32 may be affixed to plate 27 by any suitable means such as welding. There are four such plates 32 shown, each one located concentrically over one of the four outermost reamed holes 29. It should be evident that additional plates 32 could be provided over each hole 29 and that each plate 32 has a concentrically located hole which aligns with holes 29 and allows insertion of one of the load cells 31. Though the preferred embodiment depicts the use of two load cells, one located at each of the oppositely located outermost reamed holes 29, the use of more load cells for greater accuracy or at different positions along the lateral centerline could be used. Scale adjustments would, of course, have to be made when interpreting the electrical signals produced by the load cells because their lateral distance from the center of rotation affects the moment of the rotational force, i.e., the measured torque.

Each load cell 31 includes a segmented cutout 33 at the periphery of the load cell 31 head. A keeper plate 34 is affixed to plate 32 and/or plate 27, by any suitable means such as bolts 35, in such a manner that when load cell 31 is inserted through plates 32 and 27, keeper plate 34 interlocks with cutout 33 to prevent any turning or rotary motion of the load cell during testing. Rectangular plate 32 positions the load cell at sufficient height for insertion of keeper plate 34. The function and operation of the load cells will be more clearly set forth hereinafter during the discussion of operation of the overall apparatus.

A lower saddle assembly is generally indicated by the numeral 36 and consists of a generally rectangular flat plate 37 with two generally square shaped guide rails 38. The guide rails are disposed along the outer lateral perimeter of plate 37 but not quite flush with the edges of plate 37. A plurality of bronze pads 39 are disposed on the top side of plate 37, one near each corner and one in the center. A lower saddle hub 40 is concentrically affixed, such as by welding, to the bottom side of plate 37 and may be bored and keyed similar to hubs 21 and 22 so as to accept shaft 41 by methods well known in the art. It will be noted that there is no direct mechanical coupling between hub 21 and hub 40, except through the load cells 31, and as best shown in FIG. 5 the hubs are driven by separate shafts 19 and 41, respectively. A pair of gussets 42 may be affixed laterally on the bottom side of plate 37 on either side of hub 40 to provide mechanical strength to plate 37. Plate 37 also has a plurality of reamed holes 43 with bushings, disposed along the lateral center line of plate 37, and of the same dimensions as the holes 29 and bushings 30 in upper saddle assembly 26 such that when the upper saddle assembly 26 is affixed to the lower saddle assembly 36 the respective holes 29 and 43 are aligned to allow insertion of load cells 31.

Disposed between upper saddle assembly 26 and lower saddle assembly 36 is sensor bar assembly 44. Sensor bar assembly 44 includes a flat plate 45 and concentrically mounted torque sensor bar hub 21 as previously described. Plate 45 has a plurality of reamed holes 46 and hardened bushings, disposed along its lateral center line and of the same dimensions as the holes 29 and bushing 30 in upper saddle assembly 26 such that when upper saddle assembly 26, sensor bar assembly 44 and lower saddle assembly 36 are assembled together, all the holes 46, 43 and 29 at the respective locations are aligned so as to allow insertion of load cells 31.

Assembly of torque sensor bar assembly 25 may be accomplished by placing sensor bar assembly 44 between rails 38 on lower saddle assembly 36 such that plate 45 rests on bronze pads 39. Pads 39 allow plate 45 to sit flat during assembly to prevent the same from warping or bending under its own weight. Sensor bar assembly 44 is positioned such that holes 46 are aligned with holes 43 in lower saddle assembly 36. To simplify alignment during assembly, dummy pins of the same diameter as load cells 31 may be temporarily inserted in holes 43 and then through holes 46. Upper saddle assembly 26 may next be placed on top of lower saddle assembly 36 and affixed thereto by any suitable means such as capscrews 48 which cooperate with holes 49 in rails 38, such that hub 21 protrudes up through cutout 28 in upper plate 27. After upper assembly 26 is firmly affixed to lower assembly 36 the temporary alignment pins can be removed through holes 29. Load cells 31 are then inserted through the barrels formed by holes 29, 46 and 43. Keeper plates 34 are then installed for each load cell 31 as described previously to prevent rotation of load cells 31.

Figure 6:
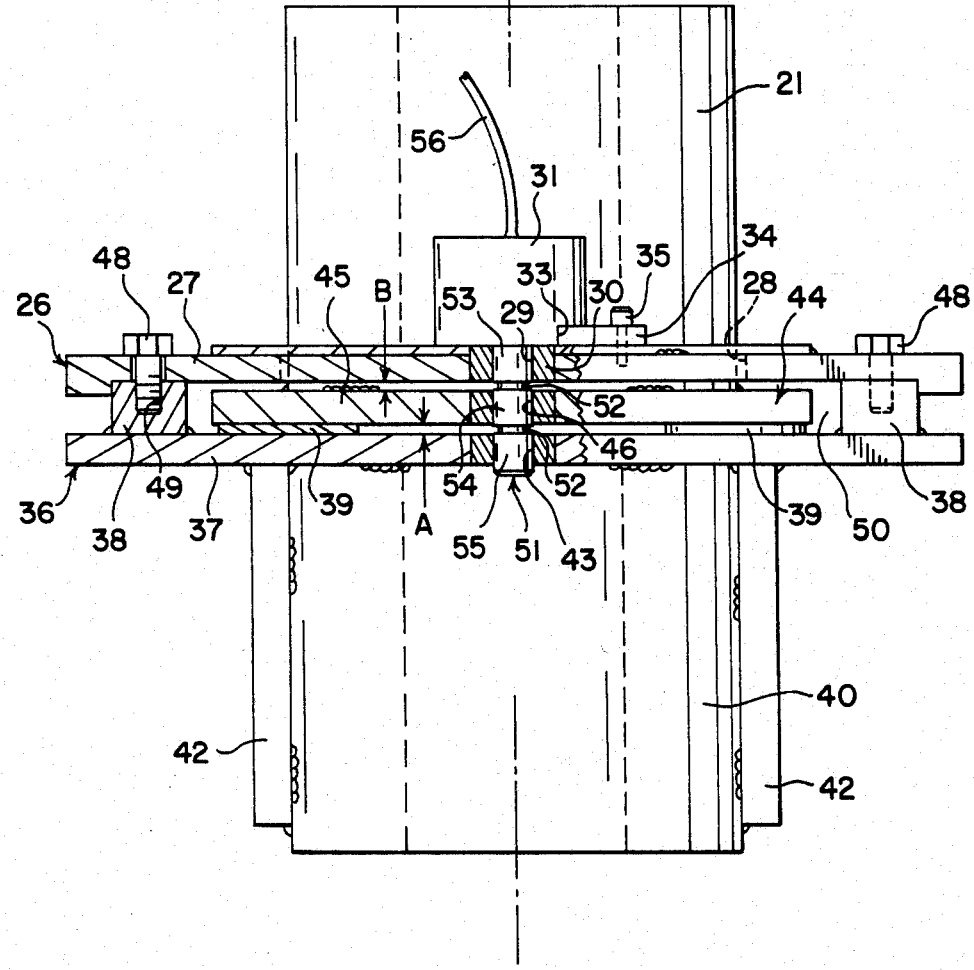
FIG. 6 is a sectional view of an assembled torque sensor bar assembly taken substantially along line 6—6 of FIG. 5.

FIG. 6 shows torque sensor bar assembly 25 after complete assembly. It will be appreciated by one skilled in the art that guide rails 38 are disposed not quite to the edges of plate 37 such that when upper saddle assembly 26 is affixed to lower saddle assembly 36, "C" plate 27 interlocks over rails 38. Thus, assemblies 26 and 36, when mated, form a channel 50 between them with sensor bar 45 disposed therein. As described previously, sensor bar plate 45 rests on bronze pads 39 resulting in clearance "A" between plate 45 and plate 37 and clearance "B" is allowed between plate 45 and upper saddle assembly 26.

Load cells 31 may be conventional strain gauge devices such as are manufactured by Strainsert, West Conshohocken, Pa. Load cells 31 have strain gauges sealed inside small axial holes in pin 51 and are located at two different depths corresponding to zones 52 in FIG. 6. The strain gauges are electrically connected to form a full bridge, the signal from each gauge being additive so that the bridge output is proportional to the sum of the loads transmitted at the two shear planes of pin 51. Load cells 31 are positioned in the torque sensor bar assembly 25 in such a manner as to be loaded in the load sensing areas 52. Keeper plates 34 (FIG. 5) prevent cell 31 from rotating and from being loaded in a non-sensing area of pin 51. Pin 51 is journalled and as shown in FIG. 6, the top journal 53 is engaged by upper saddle assembly 26; the middle journal 54 is engaged by sensor bar plate 45 and the bottom journal 55 is engaged by lower saddle assembly 36. Thus, the load sensing areas 52 of cell 31 are positioned within clearances "A" and "B" on either vertical side of plate 45. Since only upper saddle assembly 26 and lower saddle assembly 36 are mechanically interlocked as by rails 38, sensor bar plate 45 is mechanically coupled to assemblies 26 and 36 only by load cells 31. Thus, load cells 31 measure a shear force load effect when torsion is applied to hub 21 and hub 40. By way of example only, if a clockwise torque is applied to hub 21 and a counterclockwise torque of equal magnitude is applied to hub 40 (remembering that hub 21 and hub 40 are independently actuated), load cells 31 will be under load and will generate electrical signals proportional to the shear forces acting on load sensing areas 52. These electrical signals are carried by a wire 56 from each load cell 31.

The torque applied to hubs 21 and 40 is directly and accurately coupled to the load cells 31. Of course, load cells 31 only sense the shear force load applied to them but because the distance from the center of the rotational force, that is, the center of hub 21 and hub 40 to the load cell 31, can be measured, torque can be accurately calculated as the moment of the force measured at a known radius, a principal well known to one of ordinary skill in the art. Thus torque sensor bar assembly 25 provides an accurate and simplified method and apparatus for measuring an applied torque with minimal error induced by the coupling means from the torque source to the sensing elements.

Referring back to FIG. 3, torque fixed plate 16 is affixed to main frame 10 as previously described. A suspended plate 57 depends from plate 16 as by four suspension cables 58 by methods well known to one skilled in the art, each one located at approximately each corner of plate 57. Two links 59 are movably affixed to plate 57 with one end of each link affixed to plate 57 as by pins 60, located generally midway near opposite peripheral sides of plate 57. The opposing ends of links 59 are movably affixed to main frame 10 at points "C" and "D" (FIG. 2) as by pins 61. When suspended plate 57 has been movably linked to main frame 10 and suspended from fixed plate 16 as described, plate 57 is free to move in a lateral motion orthogonal to the peripheral sides of plate 57 to which links 59 are pinned. In the exemplary embodiment depicted in FIG. 3 this would be a left/right movement. It should be noted, however, that links 59 prevent any undesirable rotary motion of plate 57.

A torque actuator plate 62 is nested in a cutout 63 in plate 57. A clearance 64 is allowed between plate 62 and plate 57 when it is nested within cutout 63. Torque actuator plate 62 also depends from fixed plate 16 as by suspension cables 65 which are mounted on "C" channels 66 affixed to opposing ends of plate 62. Any portion of channels 66 which extends over plate 57 should not contact plate 57 so as to allow lateral movement of plate 62 relative to plate 57. A second pair of links 67 are movably affixed at one end near opposite peripheral sides of plate 62 as by pins 68; and the opposite ends of links 67 are movably affixed to plate 57 as by pins 69 so that when plate 62 has been movably linked to plate 57 and suspended from plate 16, plate 62 is free to move in a lateral motion orthogonal to the direction of movement determined by links 59, and the degree of movement of plate 62 relative to plate 57 will be determined by the amount of clearance 64 allotted for between plates 57 and 62. All pinned joints 60, 61, 68 and 69 may be equipped with hardened pins and self-aligning bearings well known to one skilled in the art to minimize any friction between the pins and links.

Torque actuator plate 62 includes a torque actuator mounting ring 70 concentrically affixed thereto by any suitable means such as bolts. Plate 62 and ring 70 each have a concentrically located essentially circular orifice 71 of sufficient diameter to accommodate shaft 41.

Shaft 41 includes a stop collar 72 similar to stop collar 23 on shaft 19. The portion of shaft 41 above collar 72 inserts into hub 40 on assembly 25 and the portion of shaft 41 below collar 72 extends down through orifice 71 and can be affixed to a lower torque device 73. Device 73 may be the same type device as device 20 previously described. Device 73 is affixed to the bottom of actuator mounting ring 70 by any suitable means such as bolts. As previously stated in reference to upper torque actuator 20, the particular actuator mounting assembly used with plate 62 will depend on the type of device under test. With suspended plate 57 and torque actuator plate 62 suspended from torque fixed plate 16 and pinned to main frame 10 at points "C" and "D" on main frame 10, device 73 attached to this mechanism has free motion in two dimensions. The freedom of movement of device 73 minimizes or eliminates any binding that would appear trying to couple test devices 20 and 73. This elimination of binding minimizes any error in the test readings due to mechanical misalignment. Any mechanical misalignment between the two torque actuators 20 and 73 is automatically compensated for by the free two dimensional movement of the two suspended plates 57 and 62.

A secondary suspension frame is generally indicated in FIG. 4 by the numeral 74. Frame 74 includes four posts 75, one each of which is disposed near one corner of a fixed plate 76 at points "E". A pair of support beams 77 each join one pair of posts 75 such that beams 77 are generally parallel to each other. A pair of crossbeams 78 are disposed generally in parallel between beams 77 as in FIG. 4. Beams 78 provide a support frame for suspension cables 79 and 80.

Fixed plate 76 is affixed to main frame 10 by any convenient means such as bolts at locations noted "Z" in FIG. 2 such that plate 76 is carried on upper support beams 13. A suspended plate 82, supported from frame 74 by cables 79, is nested within a large concentric cutout 81 in plate 76 with sufficient clearance 83 to allow lateral movement of plate 82 therein. Plate 82 is linked to plate 76 by links 84 and pins 85 in a similar manner as plate 57 is linked to main frame 10. Movement of plate 82, therefore, relative to plate 76, is restricted to lateral movement perpendicular to the link 84 longitudinal axis.

An actuator suspended plate 86 is supported from frame 74 by cables 80. Plate 86 is, likewise, suspended such that it is nested in a cutout 87 in plate 82 with sufficient clearance to allow lateral movement. Plate 86 is linked to plate 82 by links 88 and pins 89 such that the lateral movement of plate 86 is orthogonal to the direction of lateral movement of plate 82. Again, all pin joints 85 and 89 may be equipped with hardened pins and self-aligning bearings well known to one of ordinary skill in the art.

A friction actuator mounting ring 90 may be affixed to plate 86 by any convenient means such as bolts. Ring 90 and plate 86 include concentrically located orifices 91 which are of sufficient diameter to accept a shaft 92. A friction actuator device 93 is affixed to the top of ring 90 by any suitable means such as bolts. Shaft 92 is of sufficient length to extend down through actuator 93, through orifice 91 and into a friction sensor bar hub 94. Hub 94 is part of a friction sensor assembly generally indicated by the numeral 95 which may be identical in construction to torque sensor bar assembly 25 previously described in detail. Shaft 92 may be keyed as shafts 19 and 41 and may further be flanged at the top to stop the shaft from being inserted completely into hub 94 such that sufficient endplay may be present to allow vertical adjustment of assembly 95.

It will be noted that the friction test assembly of FIG. 4 has the same two dimensional movement feature as the torque test assembly of FIG. 3 previously described. This novel feature automatically compensates for any mechanical misalignment between friction actuator 93 and the remaining apparatus, as previously described.

All load cells 31 include wires 56 which transfer the electrical signals produced by load cells 31 to a transducer unit 96. Transducer 96 converts the load cell 31 electrical signals to equivalent torque reading or friction readings as a function of the signal magnitude and lateral distance of the load cell from the center of the rotational force applied as previously described. Transducer 96 processes the load cell 31 signals by methods well known to one of oridinary skill in the art and inputs the resultant signals to digital and analog panel meters so that the test operator can record the appropriate torque and friction readings. Transducer 96 may include its own power supply, amplifiers, strain gauge conditioners and calibration instrumentation all known to one of ordinary skill in the art. It is contemplated that variations in methods of measuring and recording the data produced during the tests are possible and within the scope of the present invention.

The operation of the apparatus according to the present invention will be described, by way of example only, as used to make torque and friction measurements on conventional valve actuators, however, the method and apparatus herein disclosed as the best known embodiment of the present invention are adaptable to many different types of torque actuators and may be so used by one of ordinary skill in the art.

The two torque test actuators 20 and 73 as well as friction test actuator 93 are installed as previously described. Thereafter, the apparatus automatically compensates for any minor radial misalignment by self-alignment of the suspended plates 57, 62, 82 and 86 such that zero torque is applied to the sensor bars in the friction sensor and torque sensor assemblies. By use of the conventional calibration circuits in transducer 96 the initial readings from the load cells can be zeroed.

Equal but opposite torque is induced in both test actuators 20 and 73, for example actuator 20 in a clockwise direction and actuator 73 in a counterclockwise direction, so that the actuators maintain a stalled condition (non-rotating). Because the apparatus is self-compensating, so as to prevent binding interaction between the apparatus and test devices, and because a mechanical linkage between the two test actuators is effected through the load cells 31 as previously described, the torque output of the actuators is fully applied to the load cells 31 solely as a shear force. By measuring the shear force and knowing the moment arm through which this force is applied to the load cells, torque can be computed. The transducer unit 96 receives the load cell 31 output signals and converts them to torque readings by methods well known in the art. Thus, the developed torque of the test actuators is determined with minimal induced error due to the test apparatus.

It will be appreciated by one of ordinary skill in the art that an actuator of unknown torque characteristics could be tested by inducing a variable torque in actuators 20 and 73. Where the torque characteristics of one actuator are known, the torque can be variably applied to each actuator until a stall condition is achieved. The readings from sensors 31 would then indicate the torque output of the actuator with a previously unknown torque characteristic.

Friction tests when the actuator is energized can be performed at various load conditions. Friction test actuator 93 is installed as previously described. The test actuators 20 and 73 are actuated with specific test torques and, as stated, maintained under a load in a stalled condition (neither actuator turning though under pressure). When additional torque is induced by friction actuator 93 it thereby causes both test actuators 20 and 73 to rotate as the torque developed by friction actuator 93 is coupled through shaft 92, through the load cells 31 in friction sensor assembly 95 to shaft 19 and thereafter to the torque test actuators 20 and 73 as previously described. Because friction sensor assembly 95 consists of load cells 31 at a known radius from the neutral axis of all three actuators, the shear load exerted on load cells 31 in assembly 95 can be measured from the electrical signals produced by load cells 31 and converted by transducer 96 to friction readings. Friction sensor assembly 95 measures the total friction resisting rotary motion of the test actuators during a test. The assumption that both test actuators 20 and 73 have the same friction may be made if actuators 20 and 73 are the same type. As such, the output signal indicative of friction must be divided by two in order to determine the friction of each of the test actuators. This rotary motion method allows a break-away friction (force required to start the stalled test actuators 20 and 73 rotating) and a dynamic friction (force required to maintain turning of the two stalled test actuators 20 and 73) measurement to be made. Thus the apparatus and method herein disclosed allow torque and friction measurements to be made on the same apparatus, including break-away and dynamic friction measurements under different load settings, independent of mechanical misalignment, binding or undesirable force contributions of the test apparatus.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that an apparatus constructed according to and method embodied within the concept of the present invention, and reasonably equivalent thereto, will accomplish the objects of the present invention and otherwise substantially improve the art of measurement and utilization of material transmittance characteristics.

We claim:

1. An apparatus for measuring torque generated by devices comprising:
   a first shaft having a first torque applied thereto by a first device;
   a second shaft having a second torque applied thereto by a second device, the second torque opposing the first torque;
   sensor means for detecting forces generated by the torques of said first and second shafts respectively and providing electrical signals proportional thereto;
   means for transferring the force generated by the first torque from said first shaft and the force generated by the second torque from said second shaft to said sensor means, said means for transferring including a first plate attached to said first shaft and a second plate attached to said second shaft, said first plate and said second plate applying the forces generated by the torque from said first and said second shafts respectively to said sensor means; and
   suspension means to permit the second device to move laterally independently of the first device.

2. The apparatus according to claim 1 wherein said second plate includes means along its outer perimeter to form a channel, said first plate being disposed within said channel; wherein said means for transferring further includes a third plate covering said first and said second plates and is affixed to said second plate with said first plate disposed between said second plate and said third plate; all of said plates having a plurality of holes therein to accept said sensor means such that said sensor means provides the exclusive mechanical interconnection between said first plate and said second plate.

3. The apparatus according to claim 1 further comprising a stationary frame, said suspension means including a fixed plate attached to said stationary frame and carrying the first device; a suspended plate coupled to said stationary frame and free to move in a predetermined lateral direction; a mounting plate coupled to said suspended plate and free to move in a lateral direction generally orthogonal to the movement of said suspended plate; said mounting plate carrying the second device; and a plurality of cables which depend from said fixed plate and connect to said suspended plate and to said mounting plate.

4. The apparatus according to claim 3 wherein said suspended plate has a cutout therein and said mounting plate is positioned within the cutout.

5. The apparatus according to claim 3 wherein said suspension means further includes linkage means for movably coupling said suspended plate to said stationary frame and said mounting plate to said suspended plate.

6. The apparatus according to claim 5 wherein the first device and the second device are valve actuators.

7. An apparatus for measuring friction characteristics of devices comprising:
   a first shaft having torque applied thereto by a first device and opposing torque applied thereto by a second device such that zero resultant rotational moment is applied to said first shaft;
   a second shaft rotationally interrelated with said first shaft and having torque applied thereto by a third device;
   sensor means for detecting the forces generated by the torque of said third device and providing electrical signals proportional thereto, said electrical signals being related to the frictional characteristics of said first and second devices;
   means for transferring the force generated by the torque from said third device to said sensor means; and
   suspension means to permit independent lateral movement of said second device and said third device with respect to said first device.

8. The apparatus according to claim 7 wherein said means for transferring includes a first plate attached to said first shaft and a second plate attached to said second shaft, said second plate applying the forces generated by the torque from said third device to said sensor means and said first plate.

9. The apparatus according to claim 8 wherein said first plate includes means along its outer perimeter to form a channel, said second plate being disposed within said channel; wherein said means for transferring further includes a third plate covering said first and said second plates and is affixed to said first plate with said second plate disposed between said first plate and said third plate; all of said plates having a plurality of holes therein to accept said sensor means such that said sensor means provides the exclusive mechanical interconnection between said first plate and said second plate.

10. The apparatus according to claim 7 further comprising a stationary frame, said suspension means including a fixed plate attached to said stationary frame and carrying the first device; a suspended plate coupled to said stationary frame and free to move in a predetermined lateral direction; a mounting plate coupled to said suspended plate and free to move in a lateral direction generally orthogonal to the movement of said suspended plate; said mounting plate carrying the third device; and a plurality of cables which depend from said stationary frame and connect to said suspended plate and to said mounting plate.

11. The apparatus according to claim 10 wherein said suspended plate has a cutout therein and said mounting plate is positioned within the cutout.

12. The apparatus according to claim 11 wherein said suspension means further includes linkage means for movably coupling said suspended plate to said stationary frame and said mounting plate to said suspended plate.

13. The apparatus according to claim 12 wherein said devices are valve actuators.

14. An apparatus for measuring torque comprising:
   a first shaft having torque applied thereto;
   a second shaft;
   sensor means interposed between said first shaft and said second shaft for detecting forces generated by the torque on said first shaft relative to said second shaft and providing electrical signals proportional thereto; and
   means for transferring to said sensor means the force generated by the torque on said first shaft relative to said second shaft, said means for transferring including a first plate attached to said first shaft and a second plate attached to said second shaft, said first plate and said second plate being fixed relative to one another by said sensor means;

wherein said second plate includes means along its outer perimeter to form a channel, said first plate being disposed within said channel; wherein said means for transferring further includes a third plate covering said first and said second plates and is affixed to said second plate with said first plate disposed between said second plate and said third plate; all of said plates having a plurality of holes therein to accept said sensor means such that said sensor means provides the exclusive mechanical interconnection between said first plate and said second plate.

15. A method for measuring torque generated by devices employing rotatable shafts, the measurements being carried out by sensing elements associated with the rotatable shafts, comprising the steps of:
   mounting a first device to a stationary frame;
   suspending a second device from the stationary frame such that the second device is free to move laterally independently of the first device;
   applying torque from the first device to a first shaft having a first plate attached thereto;
   applying opposing torque from the second device to a second shaft having a second plate attached thereto;
   interposing sensing elements between the first plate and the second plate to measure the shear forces generated thereon by the torques and provide electrical signals proportional thereto; and
   determining the applied torque from the electrical signals.

16. The method as set forth in claim 15 wherein the step of determining the applied torque includes the steps of
   determining the distances from the sensing elements to the shafts;
   determining the magnitude of the electrical signals produced by the sensing elements; and
   calculating the torque provided by the shafts therefrom.

17. A method for measuring friction characteristics of devices employing rotatable shafts, the measurements being carried out by sensing elements associated with the rotatable shafts, comprising the steps of:
   mounting a first device to a stationary frame;
   suspending a second device from the stationary frame such that the second device is free to move laterally independently of the first device;
   applying torque from the first device to a first shaft;
   applying equal but opposing torque from the second device to the first shaft;
   suspending a third device from the stationary frame such that the third device is free to move laterally independently of the first and second devices;
   applying torque from the third device to a second shaft, the second shaft being rotationally interrelated with the first shaft;
   interposing sensing elements between the first shaft and the second shaft to measure the force generated by the torque from the third device necessary to overcome friction of the first and second devices, the sensing elements providing electrical signals proportional to the force measured; and
   determining the friction characteristics of the first and second devices from the electrical signals.

18. The method as set forth in claim 17 comprising the additional step of transferring the forces generated by the torque from the second shaft to the sensing elements including the steps of
   attaching a first plate to the first shaft;
   attaching a second plate to the second shaft;
   using the sensing elements to mechanically interlock the first plate and the second plate thereby applying a shear force to the sensing elements.

19. The method as set forth in claim 18 wherein the step of determining the friction characteristics includes the steps of
   determining the distances from the sensing elements to the shafts;
   determining the magnitude of the electrical signals produced by the sensing elements; and
   calculating the friction characteristics of the devices therefrom.

* * * * *